United States Patent [19]

Hinchliffe

[11] Patent Number: 5,554,151
[45] Date of Patent: Sep. 10, 1996

[54] SPECIMEN RETRIEVAL CONTAINER

[75] Inventor: Peter W. J. Hinchliffe, New Haven, Conn.

[73] Assignee: United States Surgical Corporation, Norwalk, Conn.

[21] Appl. No.: 313,701

[22] Filed: Sep. 27, 1994

[51] Int. Cl.$^6$ ..................................................... A61B 17/00
[52] U.S. Cl. ................................................................ 606/1
[58] Field of Search ........................ 128/749–754, 128/767, 768; 604/164, 264, 317, 327, 328, 403, 905; 606/1, 106, 108, 127; 215/2, 200, 204, 205, 208, 211, 288, 293, 300, 307, 352, 375; 206/438, 828; 232/43.1–43.5; 220/254, 375

[56] References Cited

U.S. PATENT DOCUMENTS

| | | | |
|---|---|---|---|
| Re. 15,259 | 1/1922 | Hammer | 215/317 |
| 2,840,826 | 7/1958 | Ebbesen et al. | 128/749 |
| 3,419,179 | 12/1968 | Deuschle et al. | 220/375 |
| 3,420,107 | 1/1969 | Rowett . | |
| 3,684,453 | 8/1972 | Lartigue et al. . | |
| 4,773,559 | 9/1988 | Sasaki et al. | 220/375 |
| 4,871,077 | 10/1989 | Ogden et al. | 220/254 |
| 4,902,280 | 2/1990 | Lander . | |
| 4,934,556 | 6/1990 | Kleissendorf | 220/375 |
| 4,942,966 | 7/1990 | Kemp | 215/306 |
| 5,030,206 | 7/1991 | Lander . | |
| 5,037,379 | 8/1991 | Clayman et al. . | |
| 5,074,867 | 12/1991 | Wilk . | |
| 5,127,909 | 7/1992 | Shichman . | |
| 5,131,404 | 7/1992 | Neeley et al. . | |
| 5,143,082 | 9/1992 | Kindberg et al. . | |
| 5,147,371 | 9/1992 | Washington et al. . | |
| 5,156,477 | 10/1992 | Hasegawa . | |
| 5,164,575 | 11/1992 | Neeley et al. . | |
| 5,201,716 | 4/1993 | Richard . | |
| 5,201,794 | 4/1993 | Kasai et al. . | |
| 5,215,521 | 6/1993 | Cochran et al. . | |
| 5,217,023 | 6/1993 | Langdon . | |
| 5,248,480 | 9/1993 | Greenfield et al. . | |
| 5,257,984 | 11/1993 | Kelley . | |
| 5,312,009 | 5/1994 | Ratajczak et al. . | |
| 5,336,237 | 8/1994 | Chin et al. . | |
| 5,341,816 | 8/1994 | Allen . | |
| 5,370,647 | 12/1994 | Graber et al. | 606/127 |
| 5,421,488 | 6/1995 | Ehrbar | 215/2 |

Primary Examiner—Gary Jackson
Assistant Examiner—Glenn Dawson

[57] ABSTRACT

A specimen retrieval tube for use in minimally invasive diagnostic and/or surgical procedures includes an elongated fluid impervious and, preferably, transparent tube; a first end cap positioned at the proximal end of the tube and having a main body portion with an aperture therethrough, and a capping tab flexibly attached to the main body portion, the capping tab having a plug projecting therefrom for engaging the aperture and forming a fluid tight seal therewith; and a second end cap for engagement with the distal end of said tube. The specimen retrieval container is adapted for use with a trocar cannula. During use, the tube is inserted through the cannula. A grasper may be disposed through the specimen retrieval container and used to grasp the tissue sample and move it into the bore of the tube. The tube is then withdrawn from the cannula and sealed.

13 Claims, 3 Drawing Sheets

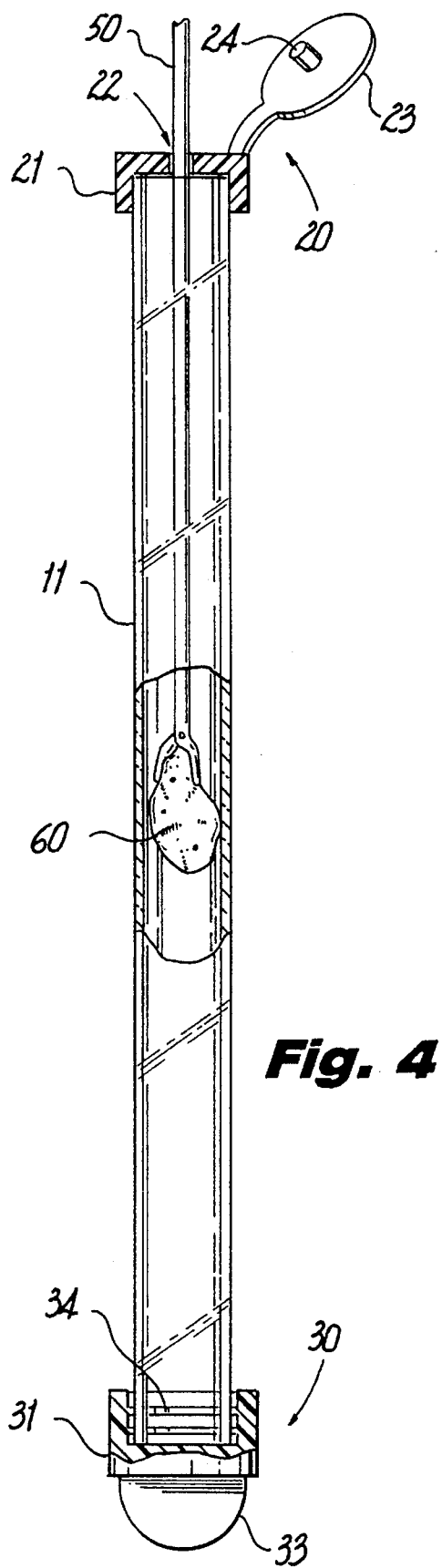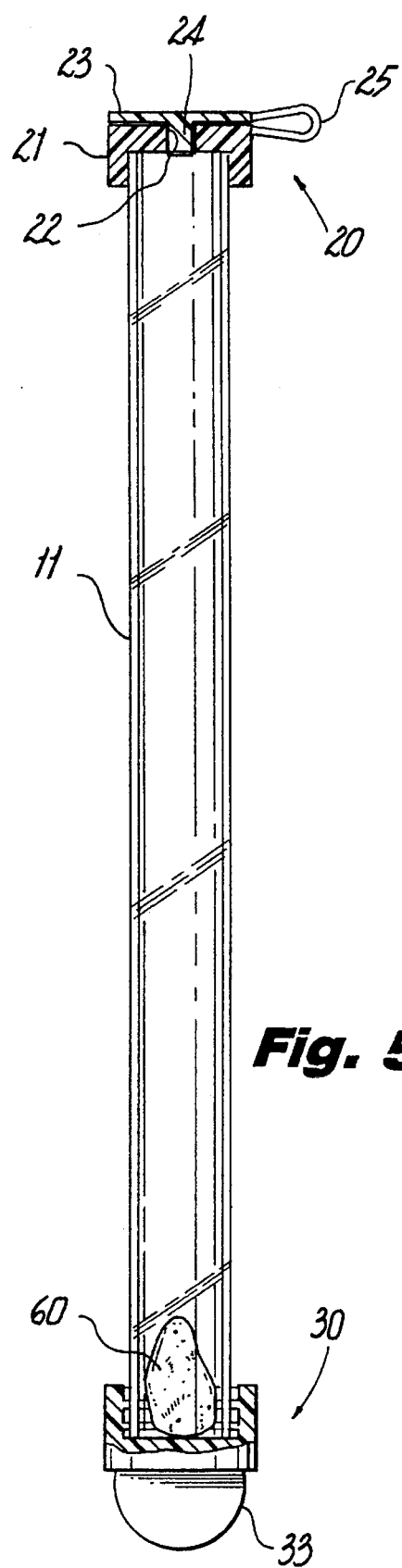

SPECIMEN RETRIEVAL CONTAINER

BACKGROUND

1. Technical Field

The present apparatus relates to a specimen retrieval container for use in minimally invasive procedures and a method for using same.

2. Background of the Related Art

Minimally invasive surgical and diagnostic procedures, such as laparoscopic (in the abdomen) and other endoscopic procedures, are carried out within the body using elongated instruments inserted through small entrance openings in the body. The initial opening in the body to allow passage of instruments to the interior of the body may be a natural passageway of the body, or it may be created by a tissue piercing instrument such as a trocar. Minimally invasive procedures are often performed in insufflated body cavities, thereby requiring that any instrumentation inserted in the body be sealed to prevent unacceptable losses in insufflatory fluid/gas, i.e. provision must be made to ensure that gases or other fluids do not enter or exit the body through the instrument or the entrance incision. Mechanical actuation of such instruments is for the most part constrained to movement of the various components along a longitudinal axis with mechanisms provided to convert longitudinal movement to lateral movement, where necessary.

In laparoscopic procedures, a cannula is typically inserted through the entrance incision to provide both a seal and a passageway for the operating instrumentation, e.g., the cannulas described in U.S. Pat. Nos. 4,902,280, 5,030,206, and 5,127,909. In most laparoscopic procedures, multiple cannulas are employed to provide access for operating instrumentation and viewing/illumination instrumentation, e.g., a laparoscope.

Minimally invasive diagnostic and surgical procedures are generally less invasive and cause less trauma to the patient as compared to procedures in which the surgeon is required to cut open large areas of body tissue. In addition, minimally invasive procedures generally allow the patient to recover more quickly, thereby reducing required hospital stays and speeding the patient's return to normal activities.

Minimally invasive procedures are often used to partially or totally remove body tissue or organs from the interior of the body, e.g. nephrectomy, cholecystectomy and other such procedures. During such procedures, it is common that a cyst, tumor, or other affected tissue or organ must be removed via the cannula. Various entrapment devices are known to facilitate this procedure.

For example, U.S. Pat. No. 5,215,521 to Cochran discloses an entrapment envelope having an apparatus for opening and closing, the apparatus being controlled from outside the body cavity. The entrapment envelope is constructed of flexible, low bulk material.

U.S. Pat. No. 5,147,371 to Washington, deceased et al. discloses a device for in situ collection of surgically excised material for removal from the body, particularly in laparoscopic and surgical procedures.

U.S. Pat. No. 5,336,237 to Chin et at. relates to a method and system for removing a specimen from a body cavity which includes an elongated expandable tubular member with a sealed interior. The tubular member is inserted through a trocar sheath and generally includes a morcellator therewithin to reduce the size of the specimen, e.g., by cutting or tearing the specimen into smaller fragments.

Other entrapment type devices for specimen retrieval in minimally invasive surgical procedures are disclosed, for example, in U.S. Pat. Nos. 5,143,082, 5,074,867, 5,037,379, and 5,156,477.

Although entrapment devices such as those mentioned above are useful, a need remains for a simpler way to remove specimens of body tissue during minimally invasive diagnostic and/or surgical procedures.

SUMMARY

A specimen retrieval container is provided herein for retrieving tissue specimens during minimally invasive diagnostic and/or surgical procedures. The specimen retrieval container includes (a) an elongated fluid impervious and, preferably, transparent tube having a proximal end, a distal end, and an axial bore extending therethrough, (b) a first end cap positioned at the proximal end of the tube and having a main body portion with an aperture therethrough, and a capping tab flexibly attached to the main body portion, the capping tab having a plug projecting therefrom for engaging the aperture and forming a fluid tight seal when inserted therethrough; and (c) a second end cap for engagement with the distal end of said tube to form a fluid tight seal therewith.

The specimen retrieval container is adapted for use with a trocar cannula. During use, the tube is inserted through the cannula such that the distal end of the tube projects beyond the cannula into a body cavity. The tube is preferably longer than the cannula so that it may be manipulated from outside the patient's body. A grasper may be disposed through the specimen retrieval container and used to grasp the tissue sample and move it into the bore of the tube. The tube is then withdrawn from the cannula and sealed to prevent entry or egress of fluid therefrom.

BRIEF DESCRIPTION OF THE DRAWINGS

FIGS. 2 to 5 are a series of side views showing a method of using the specimen retrieval container.

DETAILED DESCRIPTION OF PREFERRED EMBODIMENT(S)

Figure 1:
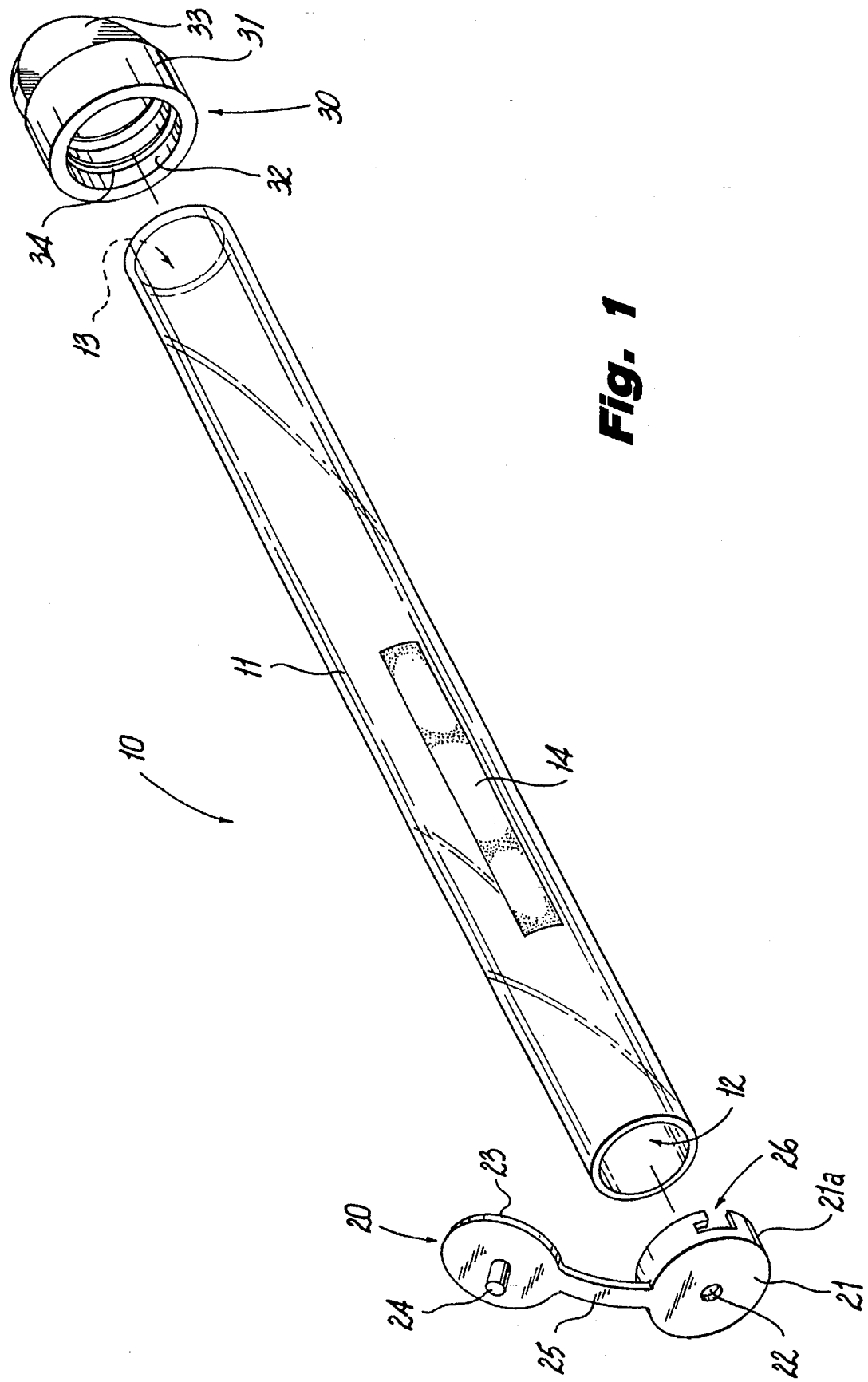
FIG. 1 is an exploded perspective view of the specimen retrieval container.

FIG. 1 illustrates the specimen retrieval container 10 which includes a tubular member 11, and two end caps 20 and 30. Tubular member 11 has an outer diameter adapted to fit within a standard trocar cannula. The tolerance between the outer diameter of the tubular member 11 and the inner diameter of the cannula is sufficiently close to provide a fluid seal yet allow for sliding movement of the tubular member 11 within the bore of the cannula. The length of the tubular member 11 should exceed the length of the cannula into which it is inserted during use. This extra length allows the tubular member 11 to be manipulated from outside the cannula end exterior to the patient's body, and it allows the distal end of the tubular member 11 to extend beyond the distal end of the cannula to prevent contact between the body tissue specimen and the cannula sheath. Typically, the diameter of the tubular member can range from about 10 to about 15 millimeters. The length of the tubular member typically ranges from about 50 to about 200 millimeters.

The tubular member 11 has an axial bore with proximal and distal end openings 12 and 13, respectively. The tubular member 11 may optionally include a labelling area 14 on the outer surface for identification purposes. The labelling area can be a frosted surface to permit writing or marking thereupon, or it can include a bar code, serial number, or other such identification device.

The tubular member 11 is fabricated from a material impervious to fluid and is preferably transparent to permit visual inspection of the contents. The fabrication material can be either rigid or flexible and optionally can also be tinted in various colors, for example, for identification purposes or to screen out certain wavelengths of light. Materials suitable for fabrication of the tubular member 11 include glass, and synthetic polymers such as acrylics, polycarbonates, polyolefins, polyurethanes and the like.

The proximal end cap 20 includes a main body portion 21 adapted to fit snugly around the proximal end opening 12 of the tubular member 11 so as to form a sealing engagement. Main body portion 21 includes a central aperture 22 aligned with the axial centerline of the tubular member 11 and preferably two or more L-shaped notches 26 positioned along side 21a for engaging corresponding projections in a cannula housing to form a bayonet type mounting system. A capping tab 23 is attached to the main body portion 21 by a strip 25. Capping tab 23 includes a plug 24 adapted to fit snugly within aperture 22 to form a fluid tight seal.

The proximal end cap 20 can be fabricated from a flexible and resilient material to provide a secure seal. Such materials as natural and synthetic rubbers, and synthetic polymers such as polyethylene, and polypropylene, and the like may be used.

The proximal end cap 20 is preferably molded as a single piece. The distal end cap 30 includes a generally cylindrical body portion 31 which is adapted to fit snugly around the distal end of the tubular member 11 to form a fluid tight seal. The cylindrical body portion 31 includes an interior chamber defined by an inner wall 32. The inner wall 32 includes circumferential ribs 34 which help to provide the fluid tight sealing contact between the inner wall 32. Optionally, the distal end cap 30 can include a gripping tab 33 projecting distally therefrom.

The distal end cap 30 may be fabricated from such materials as are described above with reference to the proximal end cap 20, and may likewise be molded as a single piece.

Figure 2:
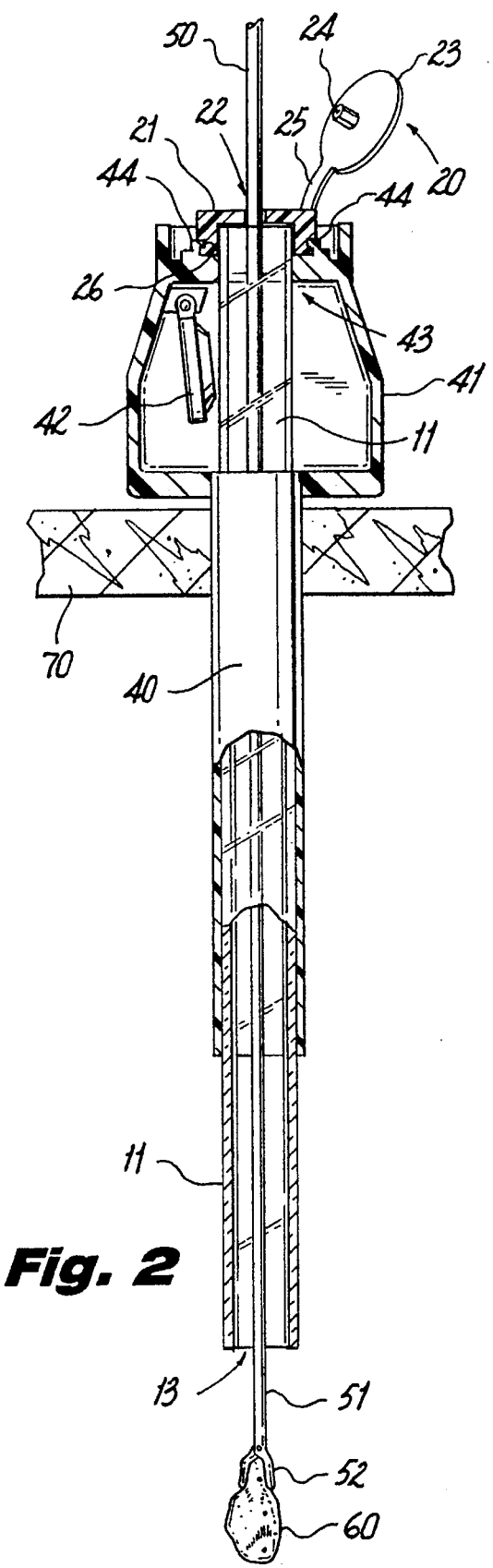

Referring now to FIGS. 2 to 5, a method for using the specimen retrieval container in a laparoscopic surgical procedure is illustrated. As shown in FIG. 2, a trocar cannula 40 is inserted through a wall of body tissue 70 into an insufflated cavity of a patient. Cannula assemblies are well known in the art, an example of which is disclosed in U.S. Pat. No. 4,943,237. The cannula assembly shown in FIGS. 2 and 3 includes a housing 41 to which the cannula 40 is fixedly attached and a pivoting flapper valve 42 which is biased to close upon a valve seat 43 to seal the cannula. Preferably, the valve seat includes two or more projections 44 for engaging corresponding notches 26 in the proximal end cap 20. Thus, the specimen retrieval container 10 is inserted through trocar cannula 40 until the main body portion 21 abuts valve seat 43 with projections 44 engaged in respective notches 26. Then, the specimen retrieval container 10 is given a short twist to lock it in place with the bayonet mounting system. The tubular member 11 extends distally beyond the distal edge of the cannula to minimize contact between the tissue specimen 60 and the distal end of the cannula 40. A grasping instrument 50 is disposed through aperture 22 of the proximal end cap 20 and through tubular member 11 into the body cavity wherein it grasps a body tissue specimen 60 which has been excised from the interior of the body during the surgical procedure. The grasping instrument 50 includes a narrow shaft portion 51 and a pair of grasping jaws 52 at the distal end thereof. A handle portion having manual actuators is not shown. Graspers useful in minimally invasive surgical procedures are well known to those with skill in the art.

Figure 3:
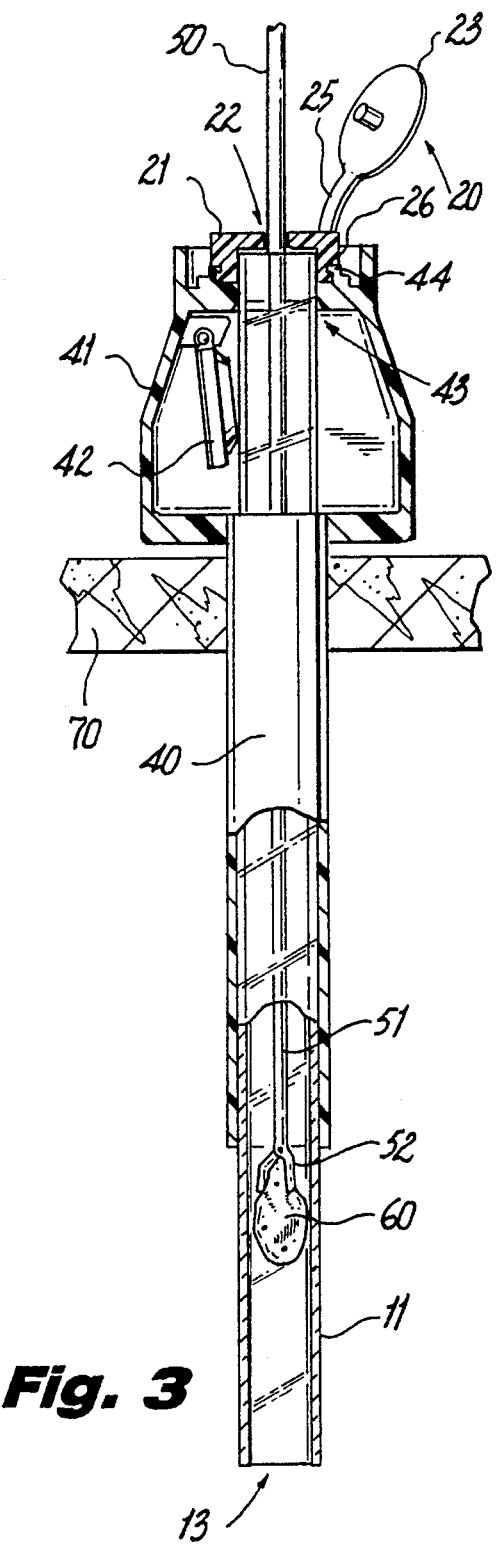

Referring to FIG. 3, the tissue specimen 60 is pulled by grasper 50 into the interior bore of tubular member 11.

Next, the bayonet mounting system is disengaged and the specimen retrieval container 10 is proximally withdrawn from the cannula.

Referring to FIG. 4, the distal end cap 30 is then positioned on the tubular member 11 to seal off distal end 13.

Referring to FIG. 5, the grasper 50 releases the body tissue specimen and is removed. The capping tab 23 is bent over to insert plug 24 through aperture 22, thereby sealing off the proximal end of the specimen retrieval tube.

The specimen may then be transported for analysis. Optionally, the proximal end cap 20 may be temporarily unplugged and fluids may be injected into the tubular member 11 to preserve or otherwise react with the specimen 60.

It will be understood that various modifications may be made to the embodiments disclosed herein. For example, various materials of fabrication other than those specifically disclosed above may be used if suitable for the purposed mentioned herein. The above description should not be construed as limiting, but merely exemplifications of preferred embodiments. Those skilled in the art will envision other modifications within the scope and spirit of the claims appended hereto.

What is claimed is:

1. A specimen retrieval container for retrieving a specimen from a body cavity, which comprises:
   a) an elongated tube having a proximal end, a distal end, and an axial bore extending therethrough, said tube being substantially impervious to fluid;
   b) a first end cap positioned at the proximal end of the tube and having a main body portion with an aperture therethrough, and a capping tab flexibly attached to said main body portion, said capping tab having a plug projecting therefrom for engaging said aperture and forming a fluid tight seal when inserted therethrough; and
   c) a second end cap releasably engaged with the distal end of said tube to form a fluid tight seal therewith, wherein said first end cap possesses at least two L-shaped notches for a bayonet type mounting engagement with a cannula assembly housing.

2. The specimen retrieval container of claim 1 wherein said tube includes a labelling area on an outer surface.

3. The specimen retrieval container of claim 1 wherein said aperture is oriented with an axial centerline of the bore.

4. The specimen retrieval container of claim 1 wherein said tube is transparent.

5. The specimen retrieval container of claim 1 wherein said tube is tinted.

6. The specimen retrieval container of claim 1 wherein said tube is substantially rigid.

7. The specimen retrieval container of claim 1 wherein said tube is flexible.

8. The specimen retrieval container of claim 1 wherein said tube is fabricated from a material selected from the group consisting of acrylic polymers, polycarbonates, polyolefins, and polyurethanes.

9. The specimen retrieval container of claim 1 wherein said second end cap includes a cylindrical portion with an interior wall, said interior wall having at least one circumferential rib.

10. The specimen retrieval container of claim 1 wherein said second end cap includes a gripping tab.

11. An assembly for retrieval of a tissue specimen from a body cavity, which comprises:
 a) a cannula for insertion into a wall of body tissue;
 b) a specimen retrieval container which includes,
  i) a tube which is slidably disposed within said cannula, said tube having a proximal end and a distal end,
  ii) a first end cap positioned at the proximal end of the tube and having a main body portion with an aperture therethrough, and a capping tab flexibly attached to said main body portion, said capping tab having a plug projecting therefrom for engaging said aperture and forming a fluid tight seal when inserted therethrough, and
  iii) a second end cap releasably engaged with the distal end of said tube to form a fluid tight seal therewith.

12. The assembly of claim 11 which further comprises:
 a grasping instrument which is slidably disposed through said aperture of said first end cap.

13. The assembly of claim 11 wherein the length of said tube is greater than the length of said cannula.

* * * * *